US012605217B2

(12) United States Patent
Oshikawa et al.

(10) Patent No.: US 12,605,217 B2
(45) Date of Patent: Apr. 21, 2026

(54) X-RAY IMAGING SYSTEM AND DEVICE DISPLAY METHOD

(71) Applicant: SHIMADZU CORPORATION, Kyoto (JP)

(72) Inventors: Shota Oshikawa, Kyoto (JP); Naoya Furuhashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 111 days.

(21) Appl. No.: 18/718,181

(22) PCT Filed: Jan. 16, 2023

(86) PCT No.: PCT/JP2023/000988
§ 371 (c)(1),
(2) Date: Jun. 10, 2024

(87) PCT Pub. No.: WO2023/153144
PCT Pub. Date: Aug. 17, 2023

(65) Prior Publication Data
US 2025/0241713 A1      Jul. 31, 2025

(30) Foreign Application Priority Data

Feb. 8, 2022      (JP) ................................. 2022-018246

(51) Int. Cl.
A61B 34/20          (2016.01)
A61B 6/12           (2006.01)
(Continued)

(52) U.S. Cl.
CPC ................ A61B 34/20 (2016.02); A61B 6/12 (2013.01); A61B 6/466 (2013.01); G06T 7/0012 (2013.01);
(Continued)

(58) Field of Classification Search
None
See application file for complete search history.

(56) References Cited

U.S. PATENT DOCUMENTS 7,646,900 B2 *    1/2010   Movassaghi ........... G06V 10/10
                                                           382/128
10,842,409 B2 *  11/2020   Hendriks .............. G06T 7/0012
(Continued)

OTHER PUBLICATIONS

Delmas, Charlotte, et al. "Three-dimensional curvilinear device reconstruction from two fluoroscopic views." Medical Imaging 2015: Image-Guided Procedures, Robotic Interventions, and Modeling. vol. 9415. SPIE, 2015.
(Continued)

*Primary Examiner* — Marcus H Taningco
(74) *Attorney, Agent, or Firm* — Muir Patent Law, PLLC

(57) ABSTRACT

The X-ray imaging system generates a three-dimensional model of a device based on a first X-ray image and a second X-ray image. The X-ray imaging system determines an inaccurate portion of the shape in the three-dimensional model (81) by identifying a parallel portion extending along a direction parallel to the epipolar line, from the device having a linear structure. The X-ray imaging system displays the three-dimensional model and a display based on the determination result of the inaccurate portion of the shape in the three-dimensional model.

7 Claims, 5 Drawing Sheets

(51) Int. Cl.

| | |
|---|---|
| *A61B 6/46* | (2024.01) |
| *G06T 7/00* | (2017.01) |
| *G06T 17/00* | (2006.01) |
| *A61M 25/01* | (2006.01) |

(52) U.S. Cl.
CPC ...... *G06T 17/00* (2013.01); *A61B 2034/2065* (2016.02); *A61M 2025/0166* (2013.01); *G06T 2207/10116* (2013.01); *G06T 2207/30168* (2013.01); *G06T 2210/41* (2013.01)

(56) References Cited

U.S. PATENT DOCUMENTS

| | | | | |
|---|---|---|---|---|
| 2002/0114423 A1* | 8/2002 | Grass | ................... | A61B 34/20 |
| | | | | 378/4 |
| 2005/0245814 A1* | 11/2005 | Anderson | ........... | G01R 33/287 |
| | | | | 600/410 |
| 2013/0211244 A1* | 8/2013 | Nathaniel | .............. | A61B 34/20 |
| | | | | 600/424 |

OTHER PUBLICATIONS

Written Opinion by the International Searching Authority for PCT application No. PCT/JP2023/000988 dated Mar. 28, 2023.

* cited by examiner

Move in the CAU direction

Start

Perform X-ray imaging — 301

Generate X-ray images — 302

Generate a three-dimensional model — 303

Determine the inaccurate portion in the shape of the three-dimensional model — 304

Display the three-dimensional model and a display based on the determination result — 305

End

X-RAY IMAGING SYSTEM AND DEVICE DISPLAY METHOD

TECHNICAL FIELD

The present invention relates to an X-ray imaging system and a device display method, and more particularly to an X-ray imaging system that displays a three-dimensional model of a device and a device display method.

BACKGROUND ART

Conventionally, a technique for generating a three-dimensional curve of a device is known. Such a technique is described, for example, in Charlotte Delmas, Marie-Odile Berger, Erwan Kerrien, Cyril Riddell, Yves Trousset, et al, "Three-dimensional curvilinear device reconstruction from two fluoroscopic views." SPIE, Medical Imaging 2015: Image-Guided Procedures, Robotic Interventions, and Modeling, February 2015, San Diego, CA, United States. San Diego, CA, United States. pp. 94150F, 10.1117/12.2081885. hal-01139284 (hereafter referred to as Non-Patent Document 1).

The above-described Non-Patent Document 1 discloses a technique for generating a three-dimensional model of a curvilinear device, such as a guidewire and a catheter, inserted into a blood vessel of a subject. Specifically, the above-described Non-Patent Document 1 discloses a technique for reconstructing a three-dimensional curve representing a device from two fluoroscopic images captured by X-ray imaging from two different imaging angles.

PRIOR ART DOCUMENT

Non-Patent Document

Non-Patent Document 1: Charlotte Delmas, Marie-Odile Berger, Erwan Kerrien, Cyril Riddell, Yves Trousset, et al, "Three-dimensional curvilinear device reconstruction from two fluoroscopic views." SPIE, Medical Imaging 2015: Image-Guided Procedures, Robotic Interventions, and Modeling, February 2015, San Diego, CA, United States. San Diego, CA, United States. pp. 94150F, 10.1117/12.2081885. hal-01139284

SUMMARY OF THE INVENTION

Problems to be Solved by the Invention

However, when generating a three-dimensional curve (three-dimensional model) by reconstructing the three-dimensional shape of a device placed inside a body of a subject, based on two images generated by X-ray imaging at two different imaging angles, as in the Non-Patent Document 1, there are cases in which the three-dimensional model of the device cannot be generated accurately. Specifically, since the X-ray image captured by X-ray imaging is a two-dimensional projected image, the shape in the depth direction along the X-ray irradiation axis direction cannot be determined in the X-ray image. Thus, even when two X-ray images are generated by capturing images at two mutually different imaging angles, it is not possible to determine the exact shape of the device in a plane perpendicular to both the projection planes of each of the two X-ray images. Therefore, in a device with a linear structure, in one X-ray image, in the portion where the device is positioned so that it extends along a direction parallel to the X-ray irradiation axis used to generate the other X-ray image, it is conceivable that the generated shape of the three-dimensional model of the device may be inaccurate and differ from the actual shape of the device. In this case, if a procedure such as moving a device inside a body of a subject is performed while viewing an inaccurate three-dimensional model that differs from the actual shape of the device, the accuracy of the procedure may deteriorate. Therefore, when generating a three-dimensional model of a device to be placed inside the body of the subject based on X-ray images generated by X-ray imaging at two mutually different imaging angles, it is desirable to suppress the user's perception of a shape different from that of the actual device.

The present invention has been made to solve the above problems. One object of the present invention is to provide an X-ray imaging system and a device display method which, when generating a three-dimensional model of a device to be placed inside a body of a subject based on X-ray images generated by X-ray imaging at two mutually different imaging angles, can suppress the user's perception of a shape that is different from the actual device.

Means for Solving the Problems

In order to attain the above-described object, the X-ray imaging system according to one aspect of the present invention comprises:

an imaging unit equipped with an X-ray irradiation unit and an X-ray detection unit, the X-ray irradiation unit being configured to irradiate a subject in which a device having a linear structure is placed inside a body of the subject, the X-ray detection unit being configured to detect X-rays transmitted through the subject, the imaging unit being configured to perform X-ray imaging on the subject at each of a first imaging angle and a second imaging angle, which are two mutually different imaging angles;

a three-dimensional model generation unit configured to generate a three-dimensional model of the device placed inside the body of the subject, based on a first X-ray image generated by X-ray imaging at the first imaging angle and a second X-ray image generated by X-ray imaging at the second imaging angle;

a determination unit configured to determine an inaccurate portion of a shape in the three-dimensional model of the device generated with the three-dimensional model generation unit by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a display unit configured to display the three-dimensional model of the device generated by the three-dimensional model generation unit and a display based on a determination result of the inaccurate portion of the shape in the three-dimensional model by the determination unit.

The device display method according to a second aspect of the present invention comprises:

a step of performing X-ray imaging at each of a first imaging angle and a second imaging angle, which are two mutually different imaging angles, by detecting X-rays transmitted through a subject in which a device having a linear structure is placed inside a body of the subject;

a step of generating a three-dimensional model of the device placed inside the body of the subject, based on a first X-ray image generated by X-ray imaging at the first imaging angle and a second X-ray image generated by X-ray imaging at the second imaging angle;

a step of determining an inaccurate portion of a shape in the generated three-dimensional model of the device by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a step of displaying the generated three-dimensional model of the device and a display based on a determination result of the inaccurate portion of the shape in the three-dimensional model.

Effects of the Invention

In the X-ray imaging system according to the first aspect described above and the device display method according to the second aspect described above, by identifying a parallel portion extending along a direction parallel to an epipolar line from the device having a linear structure, the epipolar line representing an X-ray irradiation axis at an imaging angle for generating the other X-ray image in one of the first X-ray image and the second X-ray image, the inaccurate portion of the shape in the generated three-dimensional model of the device is determined. Then, the generated three-dimensional model of the device and the display based on the determination result of the inaccurate portion of the shape in the three-dimensional model are displayed. Here, in a device with a linear structure that is placed inside the body of the subject, the parallel portion extending along the direction parallel to the epipolar line that represents the X-ray irradiation axis at the imaging angle used to generate the other X-ray image in one of the first X-ray image and the second X-ray image is an inaccurate portion when a three-dimensional model is generated based on the first X-ray image and the second X-ray image. Considering this point, the present invention displays the generated three-dimensional model of the device and a display based on the determination result of the inaccurate portion within the three-dimensional model. This allows the user to recognize the inaccurate portion in the displayed three-dimensional model that may have a shape different from the actual shape of the device by visually recognizing the display based on the displayed determination result. Therefore, when generating a three-dimensional model of a device to be placed inside the body of the subject based on X-ray images generated by X-ray imaging at two mutually different imaging angles, it is possible to suppress the user's perception of a shape different from that of the actual device.

4

Figure 5:
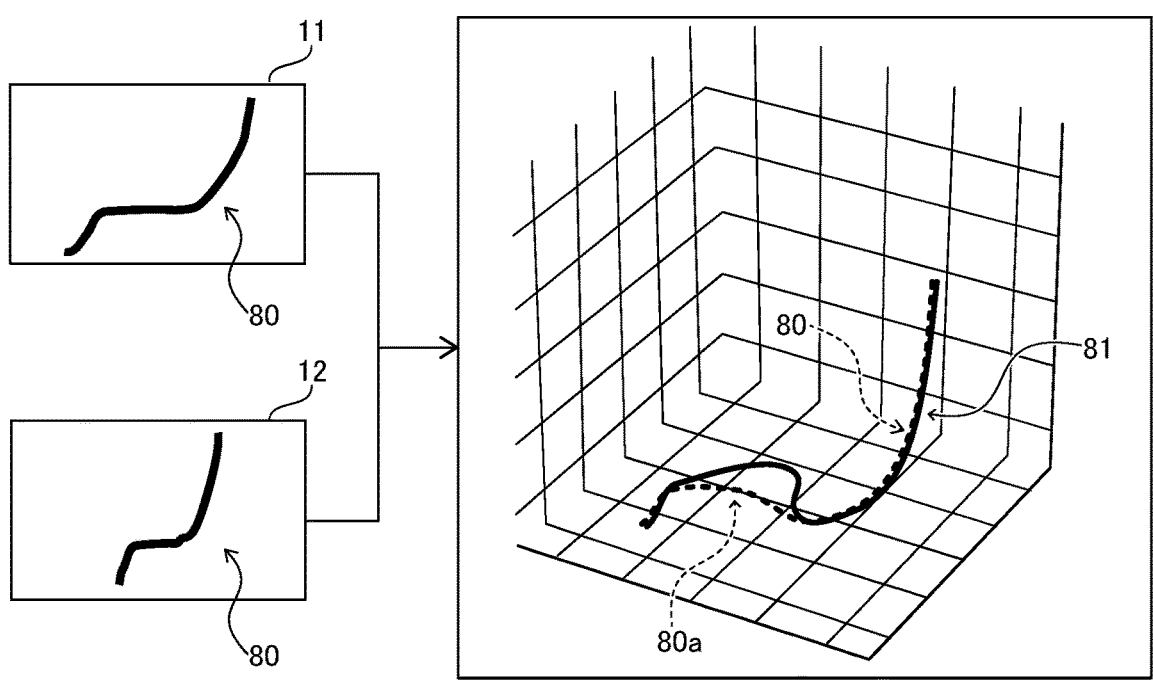

FIG. 5 is a diagram for explaining the generation of a three-dimensional model of a device.

Figure 6:
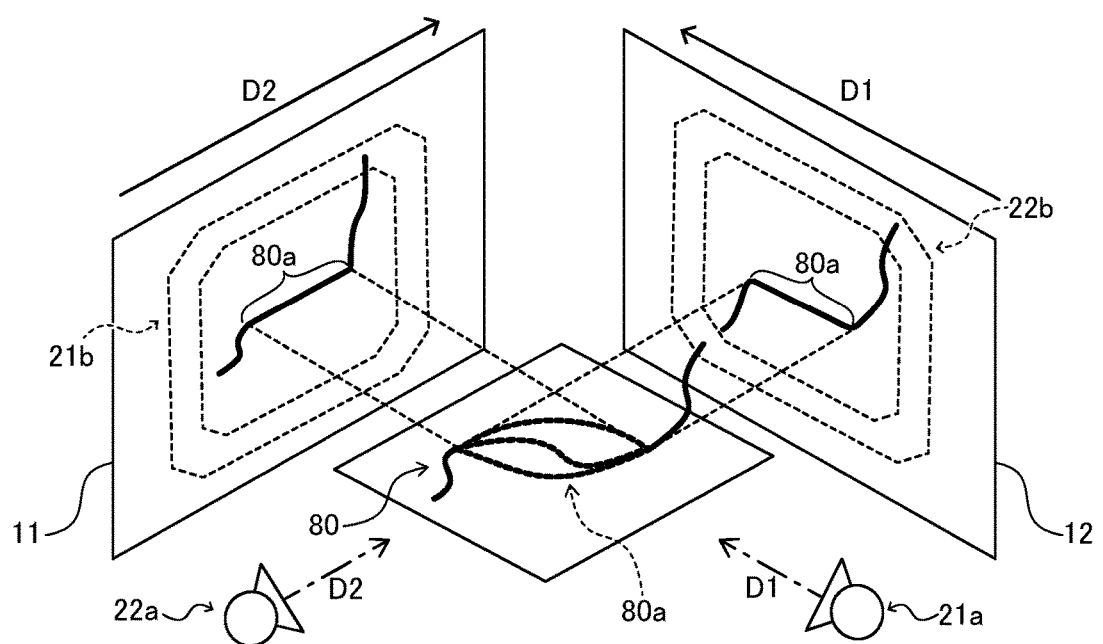

FIG. 6 is a diagram for explaining a parallel portion that extends along a direction parallel to an epipolar line.

Figure 7:
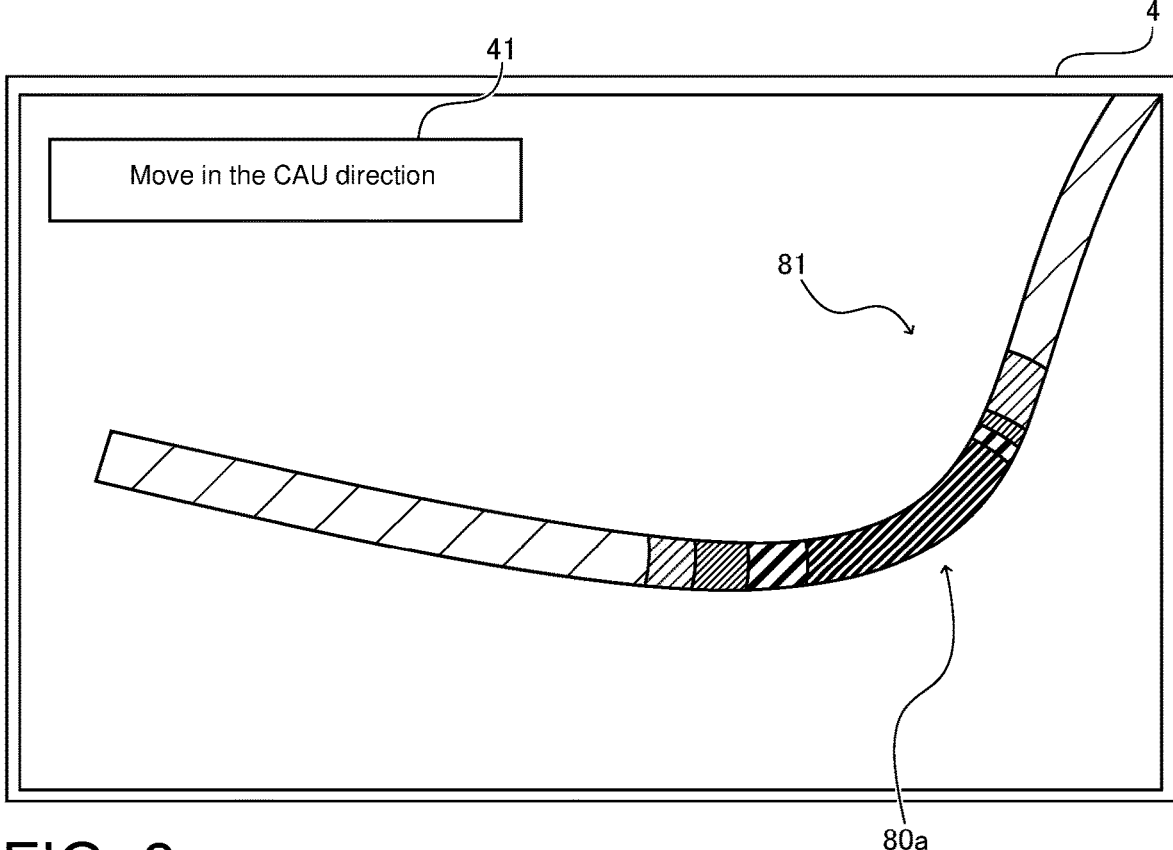

FIG. 7 is a diagram showing one example of a display on a display unit.

Figure 8:
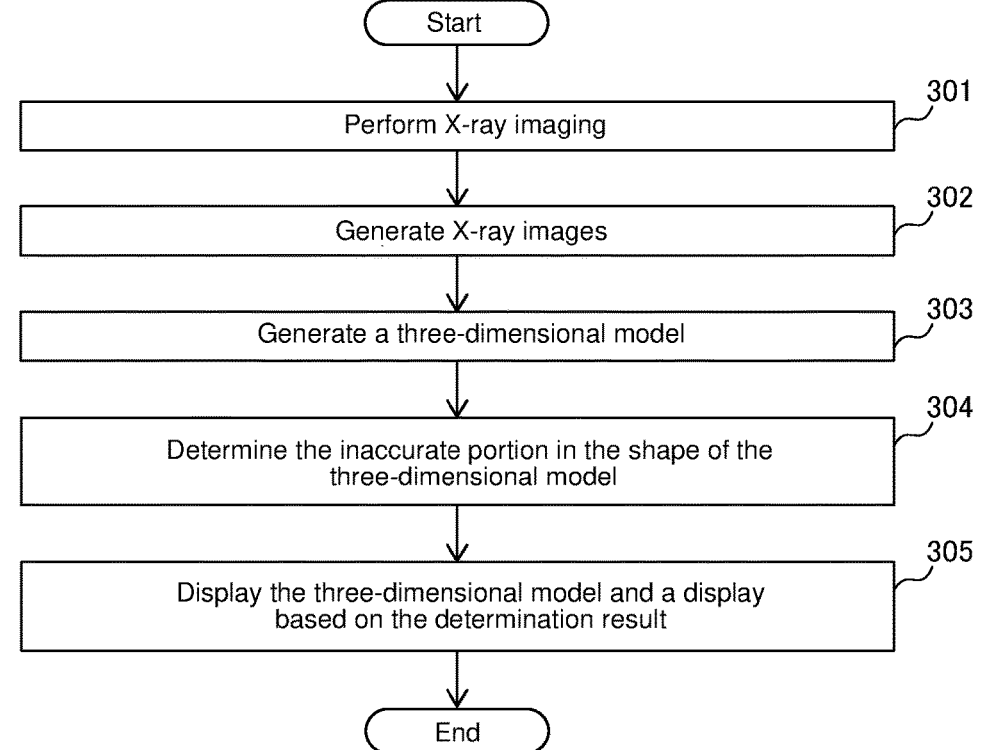

FIG. 8 is a diagram (flowchart) for explaining a device display method by an X-ray imaging system.

Figure 9:
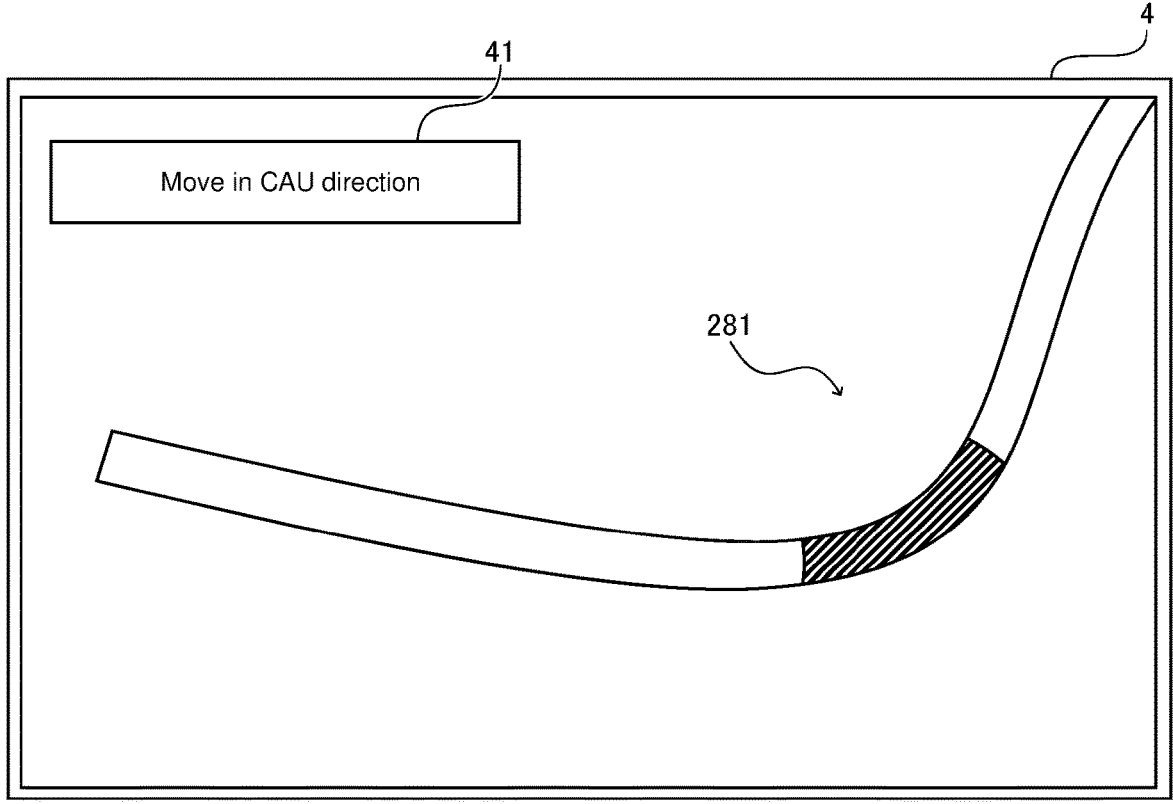

FIG. 9 is a diagram showing one example of a display of a three-dimensional model according to a modification.

EMBODIMENTS FOR CARRYING OUT THE INVENTION

Hereinafter, an embodiment in which the present invention is embodied will be described based on the attached drawings.

(Overall Configuration of X-Ray Imaging System)

Referring to FIG. 1 to FIG. 7, an X-ray imaging system 100 according to one embodiment of the present invention will be described.

Figure 1:
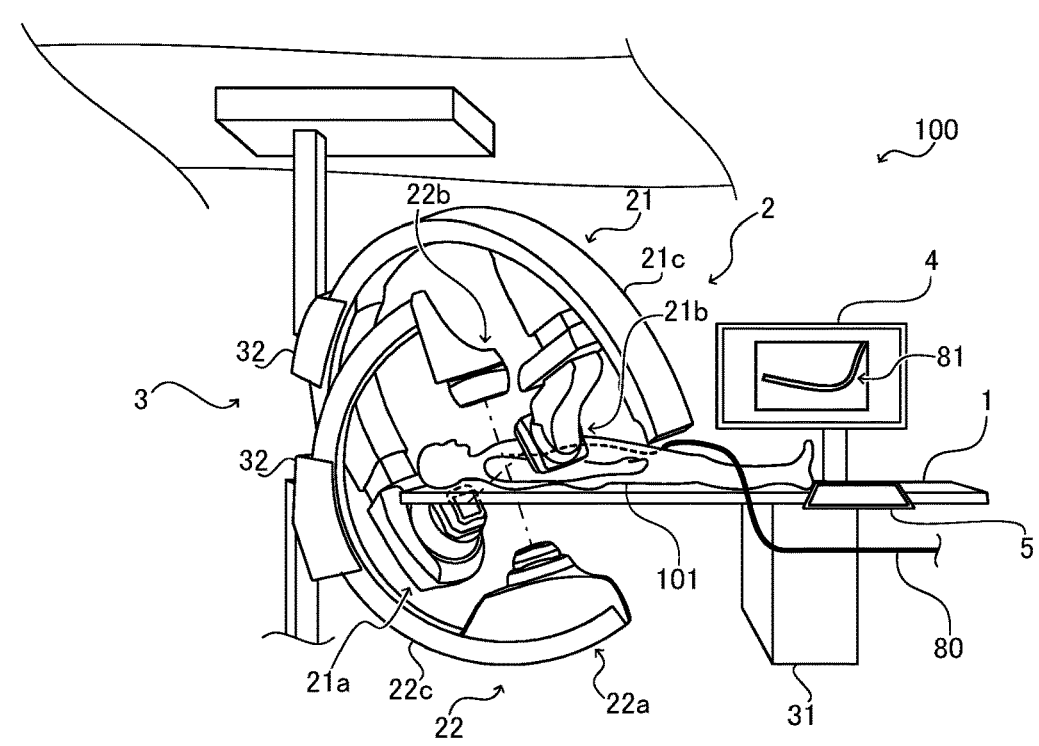
FIG. 1 is a schematic diagram showing the overall configuration of an X-ray imaging system according to one embodiment.

As shown in FIG. 1, the X-ray imaging system 100 of this embodiment irradiates a subject 101, into whose body a medical device 80 is inserted, with X-rays. The X-ray imaging system 100 performs X-ray imaging by detecting X-rays transmitted through the subject 101. The X-ray imaging system 100 generates images to observe the inside of the subject 101, for example, during Percutaneous Coronary Intervention (PCI). The percutaneous coronary intervention is a treatment for diseases caused by stenosis and obstruction of the coronary arteries of the heart, such as angina pectoris and myocardial infarction, in which the device 80 is used to relieve the stenosis and obstruction of the blood vessel.

The device 80 is, for example, a guidewire placed within a blood vessel in the body of the subject 101. The device 80 is inserted into a blood vessel for placing a catheter, a stent, or other devices inside the body of the subject 101. Further, the device 80 has a flexible linear structure so that it can be inserted into a blood vessel of a human body. The X-ray imaging system 100 according to this embodiment generates a three-dimensional model 81 of the device 80 placed inside the body of the subject 101, based on the two captured X-ray images 11 and 12 (see FIG. 4) obtained by performing X-ray imaging. The X-ray imaging system 100 is configured to display the generated three-dimensional model 81.

(Configuration of X-Ray Imaging System)

Figure 2:
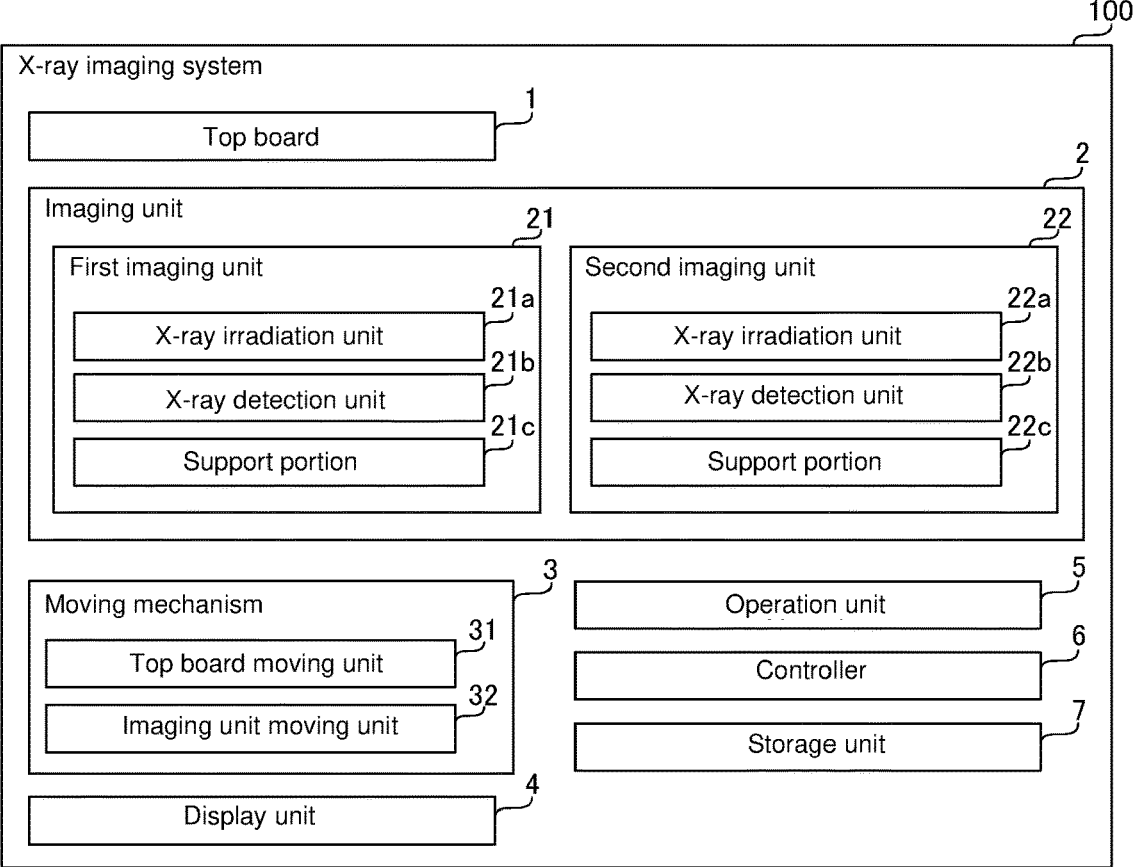
FIG. 2 is a block diagram describing the configuration of the X-ray imaging system.

As shown in FIG. 1 and FIG. 2, the X-ray imaging system 100 is equipped with a top board 1, an imaging unit 2, a moving mechanism 3, a display unit 4, an operation unit 5, a controller 6, and a storage unit 7.

The top board 1 is a bed on which the subject 101, to whom X-rays are irradiated, lies. With the subject 101 lying on the top board 1, the device 80 is inserted into the subject 101, and X-ray imaging of the subject 101 is performed. The top board 1 is configured to be movable by the top board moving unit 31, which will be described later, of the moving mechanism 3, based on the control by the controller 6.

The imaging unit 2 includes a first imaging unit 21 and a second imaging unit 22. The first imaging unit 21 includes an X-ray irradiation unit 21a, an X-ray detection unit 21b, and a support portion 21c. The second imaging unit 22 includes an X-ray irradiation unit 22a, an X-ray detection unit 22b, and a support portion 22c. The X-ray imaging system 100 is a biplane imaging apparatus equipped with two imaging mechanisms, i.e., the first imaging unit 21 and the second imaging unit 22.

Each of the X-ray irradiation unit 21*a* of the first imaging unit 21 and the X-ray irradiation unit 22*a* of the second imaging unit 22 irradiates (radiates) X-rays to the subject 101, with the device 80 placed inside the body of the subject 101. Each of the X-ray irradiation units 21*a* and 22*a* includes an X-ray tube that emits X-rays when a voltage is applied. Each of the X-ray irradiation units 21*a* and 22*a* is configured so that the intensity of the X-rays to be irradiated is controlled by controlling the voltage applied to the X-ray tube by the controller 6. Each of the X-ray irradiation units 21A and 22A performs one or more X-ray irradiations on the device 80 inside the subject 101.

Each of the X-ray detection unit 21*b* of the first imaging unit 21 and the X-ray detection unit 22*b* of the second imaging unit 22 detects X-rays transmitted through the subject 101. The X-ray detection units 21*b* and 22*b* output detection signals based on the detected X-rays to the controller 6. The X-ray detection units 21*b* and 22*b* include, for example, an FPD (Flat Panel Detector). Specifically, in the first imaging unit 21, the X-rays emitted from the X-ray irradiation unit 21*a* are detected by the X-ray detection unit 21*b*. Further, in the second imaging unit 22, the X-rays emitted from the X-ray irradiation unit 22*a* are detected by the X-ray detection unit 22*b*.

The support portion 21*c* is a C-arm that supports the first X-ray irradiation unit 21*a* and the X-ray detection unit 21*b* of the first imaging unit 21. The support portion 21*c* supports the X-ray irradiation unit 21*a* and the X-ray detection unit 21*b* so that they face each other across the top board 1 on which the subject 101 lies. Similarly, the support portion 22*c* is a C-arm support portion that supports the X-ray irradiation unit 22*a* and the X-ray detection unit 22*b* of the second imaging unit 22. Further, the support portion 22*c* supports the X-ray irradiation unit 22*a* and the X-ray detection unit 22*b* so that they face each other across the top board 1 on which the subject 101 lies. The support portion 21*c* and the support portion 22*c* are configured so that the angle (imaging angle) can be adjusted by the imaging unit moving unit 32, which will be described later, of the moving mechanism 3. Further, the support portion 21*c* is configured to allow the distance between the X-ray irradiation unit 21*a* and the X-ray detection unit 21*b* to be changed. The support portion 22*c* is configured to allow the distance between the X-ray irradiation unit 22*a* and the X-ray detection unit 22*b* to be changed.

The moving mechanism 3 includes a top board moving unit 31 and an imaging unit moving unit 32. The top board moving unit 31 changes the position and the angle of the top board 1. The top board moving unit 31 moves the top board 1 based on the control signal from the controller 6. The top board moving unit 31 includes, for example, a servo motor or a stepping motor as a driving mechanism. Further, the top board moving unit 31 outputs a signal indicating the current position and angle of the top board 1 to the controller 6.

The imaging unit moving unit 32 moves each of the first imaging unit 21 and the second imaging unit 22. Specifically, the imaging unit moving unit 32 changes the position and angle of the X-ray irradiation unit 21*a* and the X-ray detection unit 21*b* with respect to the subject 101 by moving the support portion 21*c*. Further, the imaging unit moving unit 32 changes the position and angle of the X-ray irradiation unit 22*a* and the X-ray detection unit 22*b* with respect to the subject 101 by moving the support portion 22*c*. That is, the imaging unit moving unit 32 moves the first imaging unit 21 (the X-ray irradiation unit 21*a* and the X-ray detection unit 21*b*) and the second imaging unit 22 (the X-ray irradiation unit 22*a* and the X-ray detection unit 22*b*)

to perform X-ray imaging on the subject 101 from various imaging positions and angles. The imaging unit moving unit 32 includes, for example, a servo motor or a stepping motor as a driving mechanism. Further, the imaging unit moving unit 32 outputs a signal indicating the current position and angle of the first imaging unit 21 (the X-ray irradiation unit 21*a* and the X-ray detection unit 21*b*) and a signal indicating the current position and angle of the second imaging unit 22 (the X-ray irradiation unit 22*a* and the X-ray detection unit 22*b*) to the controller 6

In this embodiment, the imaging unit 2 performs X-ray imaging on the subject 101 at each of the first and second imaging angles, which are two mutually different directions, by moving the first imaging unit 21 and the second imaging unit 22 through the imaging unit moving unit 32. Specifically, the first imaging unit 21 performs X-ray imaging at the first imaging angle. Further, the second imaging unit 22 performs X-ray imaging at the second imaging angle. The imaging angle represents the spatial angle of the X-ray irradiation axis that is irradiated onto the subject 101. In other words, the first imaging angle is the angle at which the X-ray irradiation unit 21*a* and the X-ray detection unit 21*b* face each other. In other words, the first imaging angle refers to the spatial angular direction of the irradiation axis of X-rays emitted from the X-ray irradiation unit 21*a* to the detection surface of the X-ray detection unit 21*b*, and is perpendicular to the detection surface of the X-ray detection unit 21*b*. Similarly, the second imaging angle refers to the angle at which the X-ray irradiation unit 22*a* and the X-ray detection unit 22*b* face each other and is perpendicular to the detection surface of the X-ray detection unit 22*b*. This represents the spatial angular direction of the irradiation axis of X-rays emitted from the X-ray irradiation unit 22*a* to the detection surface of the X-ray detection unit 22*b*. For example, based on the configuration where the X-ray irradiation unit 21*a* and the X-ray detection unit 21*b* are aligned vertically, the first imaging unit 21 is designed to allow the adjustment of the imaging angles. This enables the X-ray detection unit 21*b* to move in the LAO (left anterior oblique) and the RAO (right anterior oblique) directions, corresponding to the left and right directions of the subject 101, as well as in the CRA (cranial) and the CAU (caudal) directions, which are the vertical (head side and leg side) directions of the subject 101. Further, the second imaging unit 22 is similarly configured to allow the adjustment of the imaging angles, enabling the X-ray detection unit 22*b* to move in the LAO (left anterior oblique) and RAO (right anterior oblique) directions, as well as in the CRA (cranial) and CAU (caudal) directions.

The display unit 4 is, for example, a liquid crystal display or another display device. The display unit 4 displays the images (still image and moving image) generated by the controller 6. The details of the display unit 4 will be described later.

The operation unit 5 accepts input operations for operating the X-ray imaging system 100. The operation unit 5 outputs an operation signal to the controller 6 based on the accepted input operation. The operation unit 5 accepts, for example, operations to move the top board 1 and the imaging unit 2 via the moving mechanism 3. Further, the operation unit 5 accepts operations to emit X-rays for performing X-ray imaging of the subject 101. Further, the operation unit 5 accepts input operations to execute the control by the controller 6. The operation unit 5 includes, for example, a touch panel.

The controller 6 is a computer that includes components such as a CPU (Central Processing Unit), a GPU (Graphics Processing Unit), ROM (Read Only Memory), and RAM (Random Access Memory). The controller 6 controls each part of the X-ray imaging system 100 by executing a predetermined control program with the CPU. Further, the controller 6 is configured to control the operation of each part of the X-ray imaging system 100, based on the input operation received by the operation unit 5.

Figure 3:
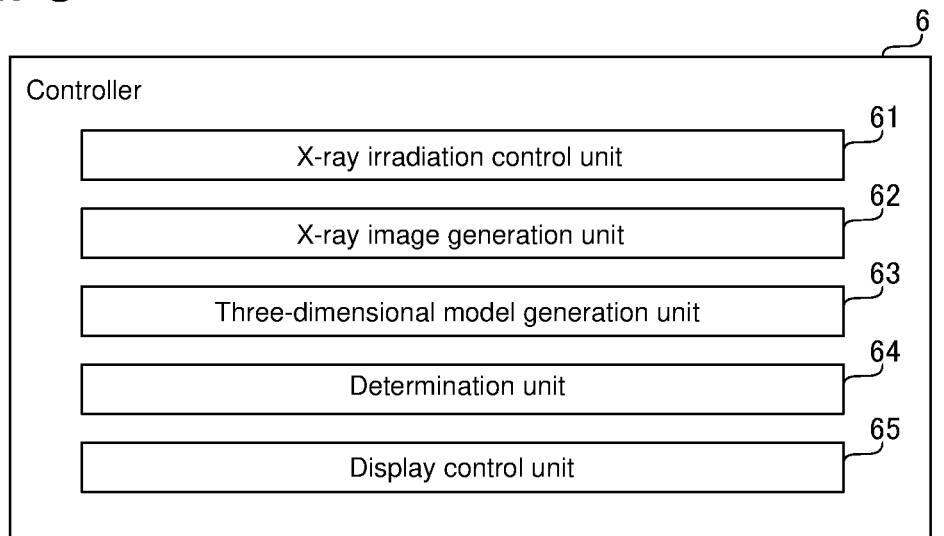
FIG. 3 is a block diagram describing the functional configuration of a controller.

Specifically, as shown in FIG. 3, the controller 6 includes, as its functional configuration, an X-ray irradiation control unit 61, an X-ray image generation unit 62, a three-dimensional model generation unit 63, a determination unit 64, and a display control unit 65. In other words, the controller 6 functions as the X-ray irradiation control unit 61, the X-ray image generation unit 62, the three-dimensional model generation unit 63, the determination unit 64, and the display control unit 65 with the CPU executing predetermined control programs. Further, the details of the control by the controller 6 will be described later.

The storage unit 7 is configured by a storage unit, such as, e.g., a hard disk drive. The storage unit 7 is configured to store image data, imaging conditions, and various settings. Further, the storage unit 7 stores programs and parameters that enable the controller 6 to function. Further, the storage unit 7 stores a trained model for detecting the device 80, used to generate a three-dimensional model 81, which will be described later.

(Control of X-Ray Imaging System by Controller)

The X-ray irradiation control unit 61 of the controller 6 controls the first imaging unit 21 (the X-ray irradiation unit 21a and the X-ray detection unit 21b) and the second imaging unit 22 (the X-ray irradiation unit 22a and the X-ray detection unit 22b) to perform X-ray imaging. Specifically, the X-ray irradiation control unit 61 controls the emission of X-rays from the X-ray irradiation units 21a and 22a by regulating the voltage applied to the their respective X-ray tubes. Further, the X-ray irradiation control unit 61 performs control to move the moving mechanism 3. Specifically, the X-ray irradiation control unit 61 controls the operation of the moving mechanism 3 to perform control to change the position and angle of the top board 1 and to change the imaging angles (the first imaging angle and the second imaging angle) of the X-ray imaging by the first imaging unit 21 and the second imaging unit 22. For example, the X-ray irradiation control unit 61 controls the moving mechanism 3 based on input operations to the operation unit 5 to change the imaging angles of each of the first imaging unit 21 and the second imaging unit 22 for X-ray imaging.

Figure 4:
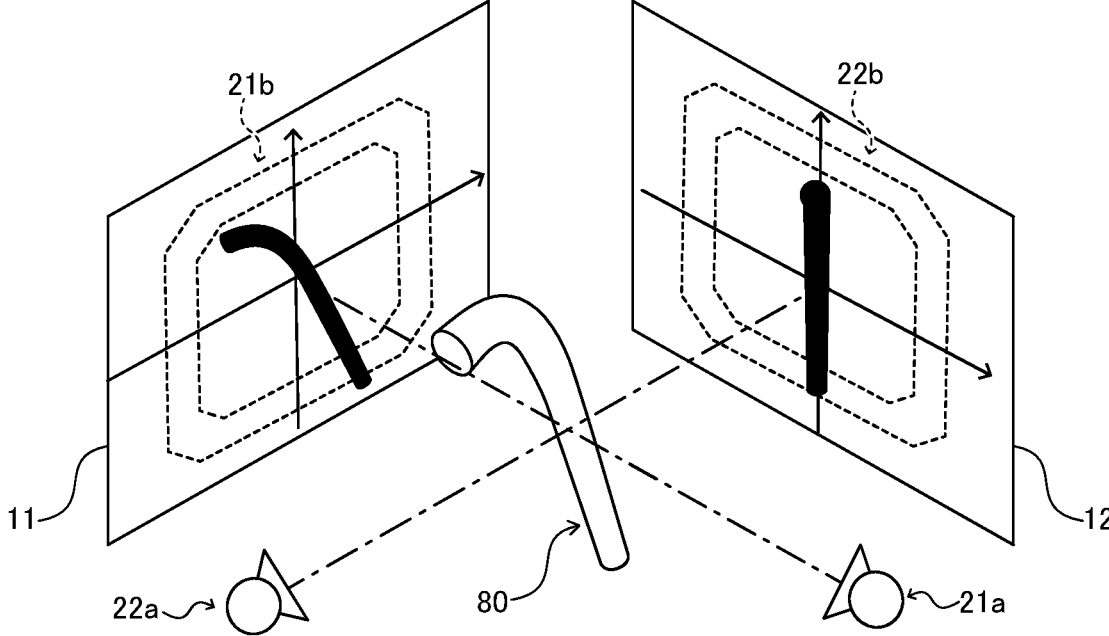
FIG. 4 is a diagram for explaining X-ray imaging of a device by a first imaging unit and a second imaging unit.

As shown in FIG. 4, the X-ray image generation unit 62 of the controller 6 generates an X-ray image 11 by performing X-ray imaging at the first imaging angle by the first imaging unit 21 (the X-ray irradiation unit 21a and the X-ray detection unit 21b), and generates an X-ray image 12 by performing X-ray imaging at the second imaging angle by the second imaging unit 22 (the X-ray irradiation unit 22a and the X-ray detection unit 22b). Specifically, the X-ray image generation unit 62 generates an X-ray image 11 based on the X-rays detected by the X-ray detection unit 21b of the first imaging unit 21. The X-ray image generation unit 62 generates the X-ray image 12 based on the X-rays detected by the X-ray detection unit 22b of the second imaging unit 22. That is, the X-ray image 11 is an image projected onto a projection plane parallel to the detection surface of the X-ray detection unit 21b, and the X-ray image 12 is an image projected onto a projection plane parallel to the detection surface of the X-ray detection unit 22b. Note that the X-ray image 11 is one example of the "first X-ray image" recited in the claims. Further note that the X-ray image 12 is one example of the "second X-ray image" recited in the claims.

FIG. 5 is a diagram for explaining the generation of a three-dimensional model of a device.

The three-dimensional model generation unit 63 of the controller 6 generates a three-dimensional model 81 of the device 80 placed inside the body of the subject 101 based on the X-ray image 11 and the X-ray image 12, as shown in FIG. 5. Specifically, the three-dimensional model generation unit 63 detects the device 80 in each of the X-ray image 11 and the X-ray image 12 based on a trained model generated by machine learning. This trained model is generated in advance by machine learning using deep learning to learn the detection processing of the position (shape) of the device 80 from the input X-ray images 11 and 12.

The three-dimensional model generation unit 63 acquires the shape information (coordinates) on the device 80 included in the X-ray images 11 and 12 by detecting the position (shape) of the device 80 in each of the X-ray images 11 and 12 using the trained model. Further, the three-dimensional model generation unit 63 acquires the imaging angles (the first imaging angle and the second imaging angle) of each of the first imaging unit 21 and the second imaging unit 22 based on the output from the imaging unit moving unit 32 in order to generate the three-dimensional model 81. The three-dimensional model generation unit 63 generates a three-dimensional model 81 of the device 80 using epipolar geometry based on the shape of the device 80 contained in each of the X-ray image 11 and the X-ray image 12 and the imaging angle of each of the first imaging unit 21 and the second imaging unit 22. In other words, the three-dimensional model generation unit 63 is configured to reconstruct the three-dimensional model 81 that estimates the shape of the device 80 in the three-dimensional space, from the device 80 contained in the X-ray image 11 and the X-ray image 12, which are projection images from two mutually different directions.

Here, as shown in FIG. 5, the shape of the generated three-dimensional model 81 may differ from the actual shape of the device 80. For example, the three-dimensional model 81 shown in FIG. 5 with solid lines differs in shape from the actual device 80 shown with dotted lines in the portion 80a. In generating the three-dimensional model 81 with imaging angles in two directions, the shape of the parallel portion of the device 80 with a linear structure that extends along a direction parallel to the epipolar line will be inaccurate. An epipolar line refers to a line that represents an X-ray irradiation axis at an imaging angle used to produce the other X-ray image in one of the X-ray image 11 and the X-ray image 12.

Specifically, as shown in FIG. 6, in the X-ray image 11, the irradiation axis direction (the direction D2) extending from the X-ray irradiation unit 22a to the X-ray detection unit 22b of the second imaging unit 22 is the epipolar line direction in the X-ray image 11. Further, in the X-ray image 12, the irradiation axis direction (the direction D1) extending from the X-ray irradiation unit 21a to the X-ray detection unit 21b of the first imaging unit 21 is the direction of the epipolar line. In other words, the direction of the epipolar line is a direction perpendicular to the respective detection surfaces of the X-ray detection unit 21b and the X-ray detection unit 22b (the respective projection surfaces of the X-ray image 11 and the X-ray image 12).

For example, the portion 80a of the device 80 shown in FIG. 6 is the portion of the X-ray image 11 that extends along the direction D2 in the X-ray image 11 and along the direction D1 in the X-ray image 12. In other words, the portion 80a is a portion (parallel portion) of the device 80 placed inside the body of the subject 101, the portion extending along a plane parallel to both the direction D1 and the direction D2. In other words, the portion 80a is a portion (parallel portion) that extends along a plane perpendicular to the projection planes of both the X-ray image 11 and the X-ray image 12. The portion 80a, which is a parallel portion, cannot uniquely determine the actual three-dimensional shape of the device 80 from the projected images, namely X-ray images 11 and 12, as illustrated by the three dotted lines in FIG. 6. In other words, the portion 80a extending along the direction parallel to the direction D2 in the X-ray image 11 and the portion 80a extending along the direction parallel to the direction D1 in the X-ray image 12 are captured as the same shape, even if their shapes in the depth direction differ in each image. Consequently, in the reconstruction of the three-dimensional model 81, the shape becomes inherently inaccurate.

[Determination of Parallel Portion]

Therefore, in this embodiment, the determination unit 64 of the controller 6 determines the inaccurate portion of the shape in the three-dimensional model 81 generated by the three-dimensional model generation unit 63 by identifying the portion 80a, which is a parallel portion extending along a direction parallel to the epipolar line, from among the device 80.

Specifically, the determination unit 64 acquires the direction of the epipolar line in each of the X-ray image 11 and the X-ray image 12 based on the signal from the imaging unit moving unit 32. The determination unit 64 compares the direction in which the device 80 extends in each of the X-ray image 11 and the X-ray image 12 with the direction of the epipolar line, based on the shape of the device 80 in the X-ray image 11 and the X-ray image 12 detected by the three-dimensional model generation unit 63. The determination unit 64 identifies the parallel portion, which is a portion extending along a direction parallel to the epipolar line, from the shape of the device 80 detected in each of the X-ray image 11 and the X-ray image 12. The determination unit 64 determines that the portion identified as a parallel portion from the device 80 is an inaccurate portion of the shape in the three-dimensional model 81.

For example, the determination unit 64 identifies the portion of the device 80 in each of the X-ray image 11 and the X-ray image 12 that has an angle difference from the epipolar line smaller than a predetermined determination threshold as being a parallel portion. Note that in the determination by the determination unit 64, in both the X-ray image 11 and the X-ray image 12, the portion where the angle difference from the epipolar line is smaller than the predetermined determination threshold may be identified as the parallel portion, or in at least one of the X-ray image 11 and the X-ray image 12, the portion where the angle difference from the epipolar line is smaller than the predetermined threshold value in at least one of the X-ray image 11 and the X-ray image 12 may be identified as a parallel portion.

[Display Control of Display Unit]

As shown in FIG. 7, the display control unit 65 of the controller 6 controls the display of the display unit 4. Specifically, the display control unit 65 causes the three-dimensional model 81 generated by the three-dimensional model generation unit 63 to be displayed on the display unit 4. Then, the display control unit 65 causes the display unit 4 to display a display based on the determination result of the inaccurate portion of the shape in the three-dimensional model 81 by the determination unit 64. Specifically, the display control unit 65 causes the display unit 4 to show the inaccurate portion of the shape in the three-dimensional model 81 determined by the determination unit 64 in an identifiable manner by coloring it as a display based on the determination result.

For example, the display control unit 65 divides the three-dimensional model 81 into a plurality of elements and displays each of the divided elements in a plurality of colors according to the angle difference from the epipolar line. For example, the display control unit 65 displays the three-dimensional model 81, which is displayed on the display unit 4, in colors such as blue, green, yellow, orange, and red, in order of the parts (elements) with the largest angle difference from the epipolar line, based on the angle difference. The part (element) of the three-dimensional model 81 that is displayed in blue is a part whose shape is estimated to be accurate in the reconstruction of the three-dimensional model 81 because of the large angle difference from the epipolar line. On the other hand, the portion (element) of the three-dimensional model 81 that is displayed in red, such as the portion 80a in FIG. 7, is a portion (inaccurate portion in shape in the three-dimensional model 81) that is determined to be a parallel portion that has a small angle difference from the epipolar line and extends along a direction parallel to the epipolar line. In other words, the parallel portion for which the angle difference from the epipolar line is determined by the determination unit 64 to be smaller than a predetermined determination threshold is colored red and displayed in the three-dimensional model 81. In FIG. 7, the differences in color coding are indicated by the differences in hatching.

Further, in this embodiment, the display control unit 65 of the controller 6 is configured to display the proposal information 41 on the display unit 4 if the determination unit 64 determines an inaccurate portion (parallel portion) of the shape in the three-dimensional model 81. The proposal information 41 is a display that suggests X-ray imaging from an imaging angle different from the first and second imaging angles so that the shape in the three-dimensional model 81 can be accurately determined. In other words, the proposal information 41 is a display that suggests changing either the first imaging angle or the second imaging angle in order to accurately estimate the shape of the parallel portion whose shape is estimated to be inaccurate in the three-dimensional model 81.

Specifically, the proposal information 41 is a display that proposes X-ray imaging at an imaging angle in a direction that intersects both the direction parallel to the first irradiation axis direction (the direction D1, see FIG. 6) at the first imaging angle and the direction parallel to the second irradiation axis direction (the direction D2, see FIG. 6) at the second imaging angle. In other words, the proposal information 41 is a display that includes a recommended movement direction for moving the imaging unit 2 so as to perform X-ray imaging at an imaging angle in a direction that intersects both the direction D1 and the direction D2. The recommended movement direction is information indicating which of the angular directions is recommended for movement, based on the current imaging angles (the first imaging angle and the second imaging angle) of the first imaging unit 21 and the second imaging unit 22 of the imaging unit 2. For example, in the example shown in FIG. 7, the proposal information 41 is displayed on the display unit 4 as character information that suggests moving the imaging units (the first imaging unit 21 and the second imaging unit 22) from the current imaging angle toward the CAU direction side. Further, the proposal information 41 may be illustrated with arrows or other symbols to show the recommended movement direction. Further, the proposal information 41 may include information suggesting which imaging angle to change, the first imaging unit 21 (the first imaging angle) or the second imaging unit 22 (the one with the second imaging angle).

As described above, in this embodiment, the display unit 4 is configured to display the three-dimensional model 81 and the coloring of the three-dimensional model 81, which is a display based on the determination result, as well as the proposal information 41, under the control of the controller 6 (the display control unit 65). The display control unit 65 of the controller 6 is configured to display the X-ray image 11 and the X-ray image 12 in addition to the three-dimensional model 81 on the display unit 4. Note that in the X-ray imaging system 100, the controller 6 generates fifteen X-ray images 11 and X-ray images 12 in one second by irradiating X-rays 15 times in one second. The display control unit 65 of the controller 6 causes the X-ray images 11 and 12 to be displayed on the display unit 4 as moving images at 15 FPS (frames per second). Similarly, the controller 6 generates a three-dimensional model 81 to be updated 15 times per second based on the X-ray images 11 and 12 generated, and causes it to be displayed on the display unit 4.

(Device Display Method)

Next, referring to FIG. 1 to FIG. 8, a device display method using the X-ray imaging system 100 according to one embodiment of the present invention will be described. Note that the control processing in Steps 301 to 305 are performed by the controller 6.

Initially, in Step 301, X-ray imaging is performed. Specifically, X-ray imaging at each of the first imaging angle and the second imaging angle, which are imaging angles in two mutually different directions, is performed by each of the first imaging unit 21 and the second imaging unit 22 by detecting X-rays transmitted through the subject 101 in which the device 80 is arranged inside the body.

Next, in Step 302, an X-ray image 11 and an X-ray image 12 are generated. Specifically, the X-ray image 11 is generated based on the X-rays detected by the X-ray detection unit 21b of the first imaging unit 21. Further, the X-ray image 12 is generated based on the X-rays detected by the X-ray detection unit 22b of the second imaging unit 22.

Next, in Step 303, a three-dimensional model 81 is generated. Specifically, a three-dimensional model 81 of the device 80 placed inside the body of the subject 101 is generated based on the X-ray image 11 captured by the first imaging unit 21 at the first imaging angle and the X-ray image 12 captured by the second imaging unit 22 at the second imaging angle.

Next, in Step 304, the inaccurate portion of the shape in the three-dimensional model 81 is determined. Specifically, an inaccurate portion of the generated three-dimensional model 81 of the device 80 is determined by identifying the parallel portion of the device 80 that extends along a direction parallel to the epipolar line.

Next, in Step 305, the generated three-dimensional model 81 of the device 80 and the display based on the determination result of the inaccurate portion of the shape in the three-dimensional model 81 are displayed. Specifically, the three-dimensional model 81 is displayed on the display unit 4. Specifically, the three-dimensional model 81 is displayed on the display unit 4. Specifically, the display control unit 65 causes the display unit 4 to show the inaccurate portion of the shape in the three-dimensional model 81 determined by the determination unit 64 in an identifiable manner by coloring it as a display based on the determination result.

Effects of this Embodiment

In this embodiment, the following effects can be obtained.

In the X-ray imaging system 100, as described above, the X-ray imaging system 100 determines the inaccurate portion of the device 80 having a linear structure from the device 80 in one of the X-ray image 11 (the first X-ray image) and the X-ray image 12 (the second X-ray image) by identifying a parallel portion that extends along a direction parallel to the epipolar line that represents the X-ray irradiation axis at the imaging angle for generating the other X-ray image. Then, the generated three-dimensional model 81 of the device 80 and the display based on the determination result of the inaccurate portion of the shape in the three-dimensional model 81 are displayed. Here, in a device 80 with a linear structure that is placed inside the body of the subject 101, the parallel portion extending along the direction parallel to the epipolar line that represents the X-ray irradiation axis at the imaging angle used to generate the other X-ray image in one of the first X-ray image 11 and the second X-ray image 12 is an inaccurate portion when a three-dimensional model 81 is generated based on the first X-ray image 11 and the second X-ray image 12. Considering this point, in this embodiment, the generated three-dimensional model 81 of the device 80 and the display based on the determination result of the inaccurate portion within the three-dimensional model 81 are displayed. This allows the user to recognize the inaccurate portion in the displayed three-dimensional model 81 that may have a shape different from the actual shape of the device 80 by visually recognizing the display based on the displayed determination result. As a result, when generating a three-dimensional model 81 of a device 80 to be placed inside the body of the subject 101 based on the X-ray image 11 and the X-ray image 12 generated by X-ray imaging at two mutually different imaging angles, it is possible to suppress the user's perception of a shape different from that of the actual device 80.

Further, in the above-described embodiment, the following further effects can be obtained by configuring as follows.

In other words, in this embodiment, as described above, the determination unit 64 (the controller 6) is configured to determine the inaccurate portion of the shape in the three-dimensional model 81 by identifying a parallel portion from the device 80 including a guidewire placed in the blood vessel of the subject 101, and the display unit 4 is configured to display a three-dimensional model 81 of the device 80 including a guidewire and a display based on the determination result of the inaccurate portion of the shape in the three-dimensional model 81 by the determination unit 64. By this configuration, when generating the three-dimensional model 81 of the device 80 including a guidewire placed in a blood vessel, the user can prevent the recognition of a shape different from that of the device 80 actually placed in the blood vessel by visually recognizing the three-dimensional model 81 displayed on the display unit 4 and the display based on the determination result of the inaccurate portion of the shape in the three-dimensional model 81. Therefore, when a user performs a manipulation such as moving the device 80 in a blood vessel while viewing the displayed three-dimensional model 81, it is possible to suppress the decrease in the accuracy of the manipulation.

Further, in this embodiment, as described above, the display unit 4 is configured to display the inaccurate portion of the shape in the three-dimensional model 81 determined by the determination unit 64 (controller 6) in an identifiable manner by coloring it. In this configuration, the user can intuitively and easily recognize the inaccurate portion in the three-dimensional model 81 by viewing the display unit 4, because the inaccurate portion in the three-dimensional model 81 is colored and displayed.

Further, in this embodiment, as described above, when the determination unit 64 (controller 6) determines the inaccurate portion of the shape in the three-dimensional model 81, the display unit 4 is configured to display a proposal information 41 that suggests X-ray imaging from an imaging angle different from the first imaging angle and the second imaging angle so that the shape in the three-dimensional model 81 can be determined. In this configuration, when there is an inaccurate portion in the generated three-dimensional model 81, the proposal information 41 is displayed, so that when changing the imaging angle to eliminate the inaccurate portion, the user can easily refer to the displayed proposal information 41 by viewing the display unit 4. As a result, the proposal information 41 can be easily referenced, and therefore the imaging angle can be easily changed to eliminate the inaccurate portion.

Further, as described above, the proposal information 41 includes the recommended movement direction for moving the imaging unit 2 so as to perform X-ray imaging at an imaging angle in a direction that intersects both the direction parallel to the first irradiation axis direction (the D1 direction) at the first imaging angle and the direction parallel to the second irradiation axis direction (the D2 direction) at the second imaging angle direction. By configuring in this way, the user can recognize the recommended movement direction proposed by viewing the proposal information 41, and can easily recognize in which specific direction the imaging angle should be changed. Therefore, the user can easily determine in which angular direction the imaging angle should be moved to eliminate inaccuracies in the three-dimensional model 81. As a result, the user can more easily change the imaging angle to eliminate inaccurate portions.

Further, in this embodiment, as described above, the imaging unit 2 includes the first imaging unit 21 that performs X-ray imaging at a first imaging angle and the second imaging unit 22 that performs X-ray imaging at a second imaging angle. The determination unit 64 (the controller 6) identifies the parallel portion extending along the epipolar line from the device 80 having a linear structure, thereby determining the inaccurate portion of the shape in the three-dimensional model 81 of the device 80 generated by the three-dimensional model generation unit 63 (the controller 6) based on the X-ray image 11 (the first X-ray image) generated through X-ray imaging by the first imaging unit 21 and the X-ray image 12 (the second X-ray image) generated through the X-ray imaging by the second imaging unit 22. In this configuration, each of the first imaging unit 21 and the second imaging unit 22 can simultaneously acquire the X-ray image 11 and the X-ray image 12 from X-ray imaging at two mutually different imaging angles. Therefore, unlike the case where the X-ray image 11 and the X-ray image 12 are acquired by performing X-ray imaging with two mutually different imaging angles in two different directions while moving one imaging unit 2, a three-dimensional model 81 can be generated in real time based on the X-ray image 11 and the X-ray image 12 while suppressing the need to move the imaging unit 2 sequentially to generate a three-dimensional model 81 in real time based on the X-ray images 11 and 12. As a result, the user can perform manipulations by viewing the three-dimensional model 81 generated in real time while suppressing the time and effort of moving the imaging unit 2, and because the display based on the determination result by the determination unit 64 is displayed, the user can recognize the portion whose shape is inaccurate in the three-dimensional model 81 generated in real time.

Effects of Image Generation Method According to this Embodiment

In this device display method, the following effects can be achieved.

In this device display method of this embodiment, by configuring as described above, from the device 80 having a linear structure, in one of the X-ray image 11 (the first X-ray image) and the X-ray image 12 (the second X-ray image), the inaccurate portion of the shape in the generated three-dimensional model 81 of the device 80 is determined by identifying the parallel portion extending along a direction parallel to the epipolar line indicating the X-ray irradiation axis at the shooting angle used to generate the other X-ray image. Then, the generated three-dimensional model 81 of the device 80 and the display based on the determination result of the inaccurate portion of the shape in the three-dimensional model 81 are displayed. Here, in a device 80 with a linear structure that is placed inside the body of the subject 101, the parallel portion extending along the direction parallel to the epipolar line that represents the X-ray irradiation axis at the imaging angle used to generate the other X-ray image in one of the first X-ray image 11 and the second X-ray image 12 is an inaccurate portion when a three-dimensional model 81 is generated based on the first X-ray image 11 and the second X-ray image 12. Considering this point, in this embodiment, the generated three-dimensional model 81 of the device 80 and the display based on the determination result of the inaccurate portion within the three-dimensional model 81 are displayed. This allows the user to recognize the inaccurate portion in the displayed three-dimensional model 81 that may have a shape different from the actual shape of the device 80 by visually recognizing the display based on the displayed determination result. As a result, when generating the three-dimensional model 81 of the device 80 to be placed inside the body of the subject 101 based on the X-ray image 11 and the X-ray image 12 generated by X-ray imaging at two mutually different imaging angles, it is possible to provide a device display method capable of suppressing the user's recognition of a shape different from the actual device 80.

Modifications

Note that the embodiments disclosed here should be considered illustrative and not restrictive in all respects. It should be noted that the scope of the invention is indicated by claims and is intended to include all modifications (modified examples) within the meaning and scope of the claims and equivalents.

For example, in the above embodiment, an example is shown in which the three-dimensional model 81 of the device 80, including a guidewire placed in the blood vessel of the subject 101, is generated; however, the present invention is not limited thereto. In the present invention, the device that generates the three-dimensional model may be a medical catheter. For example, the device that generates the three-dimensional model may be a balloon catheter for placing a stent within the subject, or a high-speed rotational coronary atherectomy (Rotational Coronary Atherectomy) for cutting a stenotic site in a blood vessel. The device may also be the stent itself.

Further, in the above embodiment, an example is shown in which the inaccurate portion of the three-dimensional model is made identifiable by coloring it with multiple colors; however, the present invention is not limited thereto. For example, as in the three-dimensional model 281 shown in FIG. 9, it may be possible to identify and display the inaccurate portion of the three-dimensional model 281 by determining that the portion where the angle difference from the epipolar line is smaller than a predetermined threshold is parallel, and by coloring only these determined parallel sections with a single color. Note in FIG. 9, the differences in color are indicated by the differences in hatching. Further, when coloring with multiple colors, the colors may be differentiated by using gradations that gradually change the hue.

Further, in the above embodiment, an example is shown in which when an inaccurate portion of the shape in the three-dimensional model 81 is detected, proposal information 41 including a recommended movement direction for adjusting from the first or second imaging angle is displayed on the display unit 4; however, the present invention is not limited thereto. For example, the proposal information may specify a specific imaging angle (e.g., LAO 30 degrees or RAO 45 degrees) instead of the angular direction of the recommended movement direction.

Further, in the above embodiment, an example is shown featuring a biplane imaging unit 2, equipped with two imaging mechanisms: the first imaging unit 21 and the second imaging unit 22; however, the present invention is not limited thereto. For example, it may be configured to generate the first X-ray image and the second X-ray image by using a single imaging unit (a set of an X-ray irradiation unit and an X-ray detection unit) to perform X-ray imaging at two mutually different imaging angles, while changing the imaging angle.

ASPECTS

It would be understood by those skilled in the art that the exemplary embodiments described above are specific examples of the following aspects.

(Item 1)

An X-ray imaging system comprising:

an imaging unit equipped with an X-ray irradiation unit and an X-ray detection unit, the X-ray irradiation unit being configured to irradiate a subject in which a device having a linear structure is placed inside a body of the subject, the X-ray detection unit being configured to detect X-rays transmitted through the subject, the imaging unit being configured to perform X-ray imaging on the subject at each of a first imaging angle and a second imaging angle, which are two mutually different imaging angles;

a three-dimensional model generation unit configured to generate a three-dimensional model of the device placed inside the body of the subject, based on a first X-ray image generated by X-ray imaging at the first imaging angle and a second X-ray image generated by X-ray imaging at the second imaging angle;

a determination unit configured to determine an inaccurate portion of a shape in the three-dimensional model of the device generated with the three-dimensional model generation unit by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a display unit configured to display the three-dimensional model of the device generated by the three-dimensional model generation unit and a display based on a determination result of the inaccurate portion of the shape in the three-dimensional model by the determination unit.

(Item 2)

The X-ray imaging system as recited in the above-described Item 1, wherein the determination unit is configured to determine the incorrect portion of the shape in the three-dimensional model by identifying the parallel portion from the device including a guide wire or a catheter, which is placed in a blood vessel of the subject, and wherein the display unit is configured to display the three-dimensional model of the device including the guide wire or the catheter and a display based on the determination result of the inaccurate portion of the shape in the three-dimensional model determined by the determination unit.

(Item 3)

The X-ray imaging system as recited in the above-described Item 1 or 2, wherein the display unit is configured to display the inaccurate portion of the shape in the three-dimensional model determined by the determination unit in an identifiable manner by coloring.

(Item 4)

The X-ray imaging system as recited in any one of the above-described Items 1 to 3, wherein the display unit is configured to display proposal information when the determination unit determines that the shape of the three-dimensional model is inaccurate, the proposal information proposing X-ray imaging from an imaging angle different from the first imaging angle and the second imaging angle so that the shape of the three-dimensional model is capable of being determined.

(Item 5)

The X-ray imaging system as recited in the above-described Item 4, wherein the proposal information includes a recommended movement direction for moving the imaging unit to perform X-ray imaging at the imaging angle in a direction that intersects both a direction parallel to a first irradiation axis at the first imaging angle and a direction parallel to a second irradiation axis at the second imaging angle.

(Item 6)

The X-ray imaging system as recited in any one of the above-described Items 1 to 5, wherein the imaging unit includes a first imaging unit that performs X-ray imaging at the first imaging angle and a second imaging unit that performs X-ray imaging at the second imaging angle, and wherein the determination unit is configured to determine the inaccurate portion of the shape in the three-dimensional model of the device generated by the three-dimensional model generation unit, based on the first X-ray image generated by X-ray imaging by the first imaging unit and the second X-ray image generated by X-ray imaging by the second imaging unit, by identifying the parallel portion extending along the epipolar line from the device having the linear structure.

(Item 7)

A device display method comprising:

a step of performing X-ray imaging at each of a first imaging angle and a second imaging angle, which are two mutually different imaging angles, by detecting X-rays transmitted through a subject in which a device having a linear structure is placed inside a body of the subject;

a step of generating a three-dimensional model of the device placed inside the body of the subject, based on a first X-ray image generated by X-ray imaging at the first imaging angle and a second X-ray image generated by X-ray imaging at the second imaging angle;

a step of determining an inaccurate portion of a shape in the generated three-dimensional model of the device by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a step of displaying the generated three-dimensional model of the device and a display based on a determination result of the inaccurate portion of the shape in the three-dimensional model.

DESCRIPTION OF REFERENCE SYMBOLS

2: Imaging unit
4: Display unit
11: X-ray image (First X-ray image)
12: X-ray image (Second X-ray image)
21: First imaging unit
21a, 22a: X-ray irradiation unit
21b, 22b: X-ray detection unit
22: Second imaging unit
41: Proposal information
63: Three-dimensional model generation unit
64: Determination unit
80: Device
81, 281: Three-dimensional model
100: X-ray imaging system
101: Subject

The invention claimed is:

1. An X-ray imaging system comprising:

an imaging unit equipped with an X-ray irradiation unit and an X-ray detection unit, the X-ray irradiation unit being configured to irradiate a subject in which a device having a linear structure is placed inside a body of the subject, the X-ray detection unit being configured to detect X-rays transmitted through the subject, the imaging unit being configured to perform X-ray imaging on the subject at each of a first imaging angle and a second imaging angle, which are two mutually different imaging angles;

a three-dimensional model generation unit configured to generate a three-dimensional model of the device placed inside the body of the subject, based on a first X-ray image generated by X-ray imaging at the first imaging angle and a second X-ray image generated by X-ray imaging at the second imaging angle;

a determination unit configured to determine an inaccurate portion of a shape in the three-dimensional model of the device generated with the three-dimensional model generation unit by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a display unit configured to display the three-dimensional model of the device generated by the three-dimensional model generation unit and a display based on a determination result of the inaccurate portion of the shape in the three-dimensional model by the determination unit.

2. The X-ray imaging system as recited in claim 1, wherein the determination unit is configured to determine the incorrect portion of the shape in the three-dimensional model by identifying the parallel portion from the device including a guide wire or a catheter, which is placed in a blood vessel of the subject, and wherein the display unit is configured to display the three-dimensional model of the device including the guide wire or the catheter and a display based on the determination result of the inaccurate portion of the shape in the three-dimensional model determined by the determination unit.

3. The X-ray imaging system as recited in claim 1, wherein the display unit is configured to display the inaccurate portion of the shape in the three-dimensional model determined by the determination unit in an identifiable manner by coloring.

4. The X-ray imaging system as recited in claim 1, wherein the display unit is configured to display proposal information when the determination unit determines that the shape of the three-dimensional model is inaccurate, the proposal information proposing X-ray imaging from an imaging angle different from the first imaging angle and the second imaging angle so that the shape of the three-dimensional model is capable of being determined.

5. The X-ray imaging system as recited in claim 4, wherein the proposal information includes a recommended movement direction for moving the imaging unit to perform X-ray imaging at the imaging angle in a direction that intersects both a direction parallel to a first irradiation axis at the first imaging angle and a direction parallel to a second irradiation axis at the second imaging angle.

6. The X-ray imaging system as recited in claim 1, wherein the imaging unit includes a first imaging unit that performs X-ray imaging at the first imaging angle and a second imaging unit that performs X-ray imaging at the second imaging angle, and wherein the determination unit is configured to determine the inaccurate portion of the shape in the three-dimensional model of the device generated by the three-dimensional model generation unit, based on the first X-ray image generated by X-ray imaging by the first imaging unit and the second X-ray image generated by X-ray imaging by the second imaging unit, by identifying the parallel portion extending along the epipolar line from the device having the linear structure.

7. A device display method comprising:

a step of performing X-ray imaging at each of a first imaging angle and a second imaging angle, which are two mutually different imaging angles, by detecting X-rays transmitted through a subject in which a device having a linear structure is placed inside a body of the subject;

a step of generating a three-dimensional model of the device placed inside the body of the subject, based on a first X-ray image generated by X-ray imaging at the first imaging angle and a second X-ray image generated by X-ray imaging at the second imaging angle;

a step of determining an inaccurate portion of a shape in the generated three-dimensional model of the device by identifying a parallel portion extending along a direction parallel to an epipolar line from the device having the linear structure, the epipolar line representing an X-ray irradiation axis at an imaging angle for generating the other X-ray image in one of the first X-ray image and the second X-ray image; and a step of displaying the generated three-dimensional model of the device and a display based on a determination result of the inaccurate portion of the shape in the three-dimensional model.

\* \* \* \* \*